United States Patent [19]

Imai et al.

[11] Patent Number: 4,920,142
[45] Date of Patent: Apr. 24, 1990

[54] FUNGICIDAL IMIDAZOLE DERIVATIVES

[75] Inventors: Tetsuya Imai, Naruto; Hisashi Takao, Tokushima, both of Japan

[73] Assignee: Otsuka Kagaku Kabushiki Kaisha, Osaka, Japan

[21] Appl. No.: 304,630

[22] Filed: Feb. 1, 1989

[30] Foreign Application Priority Data

Feb. 5, 1988 [JP] Japan ................................. 63-26274

[51] Int. Cl.$^5$ ..................... A01N 43/50; C07D 233/56
[52] U.S. Cl. ..................................... 514/399; 548/341
[58] Field of Search ......................... 548/341; 514/399

[56] References Cited

U.S. PATENT DOCUMENTS 3,991,071 11/1976 Brookes et al. ...................... 548/341

FOREIGN PATENT DOCUMENTS 50-31047 3/1975 Japan .

*Primary Examiner*—Richard A. Schwartz
*Attorney, Agent, or Firm*—Armstrong, Nikaido, Marmelstein, Kubovcik & Murray

[57] ABSTRACT

This invention provides an imidazole derivative represented by the formula

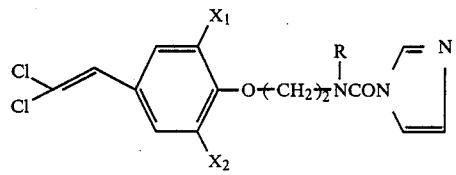

wherein R is lower alkyl, lower alkoxyalkyl, lower alkoxycarbonylmethyl or cyanomethyl, and $X^1$ and $X^2$ are each a hydrogen atom or halogen atom, process for preparing the derivative, and a fungicidal compositions comprising the derivative for use in agriculture and horticulture.

7 Claims, No Drawings

FUNGICIDAL IMIDAZOLE DERIVATIVES

The present invention relates to novel imidazole derivatives, processes for preparing the same, and fungicidal compositions comprising the derivative for use in agriculture and horticulture.

Unexamined Japanese Patent Publication No. SHO 50-31047, for example, discloses compounds, such as 1-{N-[2-(2,4-dichlorophenoxy)ethyl]-N-propylcarbamoyl}-imidazole and 1-{N-[2-(2,4,6-trichlorophenoxy)ethyl]-N-propylcarbamoyl}imidazole, which are analogous to the imidazole derivatives of the present invention. The publication states that these compounds have fungicidal activity. However, these known compounds have the problem that they are not satisfactory in fungicidal activity or cause phytotoxicity to important crops such as cereals, vegetables and fruit trees.

An object of the present invention is to provide imidazole derivatives having high fungicidal activity.

Another object of the invention is to provide imidazole derivatives which cause no phytotoxicity to important crops such as cereals, vegetables and fruit trees.

Other objects and features of the invention will become apparent from the following description.

The imidazole derivatives of the present invention are novel compounds which have not been disclosed in literature and are represented by the following formula (I).

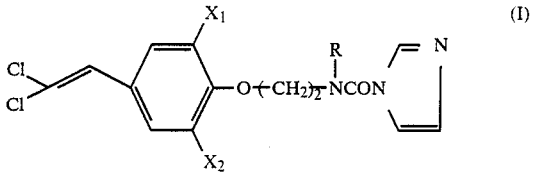

wherein R is lower alkyl, lower alkoxyalkyl, lower alkoxycarbonylmethyl or cyanomethyl, and $X^1$ and $X^2$ are each a hydrogen atom or halogen atom.

Examples of lower alkyl groups herein mentioned are alkyl groups having 1 to 6 carbon atoms, such as methyl, ethyl, n-propyl, isopropyl, n-butyl, isobutyl, sec-butyl, tert-butyl, n-pentyl and n-hexyl. Examples of lower alkoxyalkyl groups are those having 2 to 8 carbon atoms, such as methoxymethyl, methoxyethyl, methoxybutyl, ethoxymethyl, ethoxyethyl, ethoxybutyl, propyloxymethyl and butoxymethyl. Examples of lower alkoxycarbonylmethyl groups are those with an alkoxy moiety having 1 to 6 carbon atoms, such as methoxycarbonylmethyl, ethoxycarbonylmethyl, propyloxycarbonylmethyl and butoxycarbonylmethyl. Examples of halogen atoms are fluorine, chlorine, bromine and iodine atoms.

The compounds of the invention represented by the formula (I) have excellent control effects on diseases of various crops and are usable as fungicides for protecting plants without causing any undesirable phytotoxicity to crops.

The compound of the present invention can be easily prepared, for example, by the processes represented by the following reaction schemes.

Reaction scheme (1)

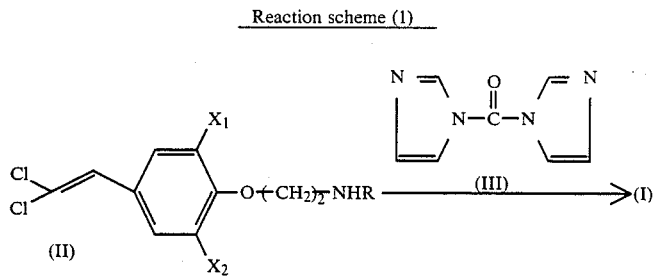

Reaction scheme (2)

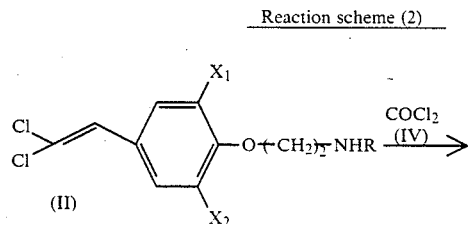

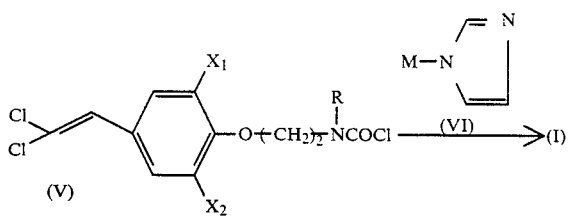

In the above schemes, R, $X^1$ and $X^2$ are as defined above, and M is a hydrogen atom or alkali metal.

The reaction represented by the scheme (1) is conducted in a solvent or in the absence of any solvent. Examples of useful solvents are ethers such as diethyl ether, dibutyl ether, tetrahydrofuran and dioxane, ketones such as acetone, methyl ethyl ketone and cyclohexanone, nitriles such as acetonitrile and propionitrile, aliphatic hydrocarbon halides such as methylene chloride, chloroform and carbon tetrachloride, aromatic solvents such as benzene, toluene and xylene, ethyl acetate, dimethylformamide, dimethyl sulfoxide, etc. The compound of the formula (II) and N,N-carbonyl diimidazole (III) are used in the ratio usually of about 1 to about 5 moles, preferably about 1 to about 3 moles, of the latter per mole of the former. It is suitable to conduct the reaction at a temperature of room temperature to about 150° C. for about 1 to about 10 hours.

With the process represented by the reaction scheme (2), the compound of the formula (II) is reacted with phosgene (IV) first to obtain carbamoyl chloride represented by the formula (V), and an imidazole (VI) is then reacted with the chloride, whereby the desired compound of the invention can be obtained. The reaction between the compound of the formula (II) and phosgene (IV) is carried out in a solvent, which is one of the solvents exemplified above for the reaction of the scheme (1). A base agent for removing hydrochloric acid is used for this reaction. Examples of useful base agents are tertiary amines such as triethylamine and diethylaniline, pyridines, etc. The compound of the formula (II) and the base agent are used in the ratio of about 1 to about 10 moles, preferably about 1 to about 5 moles, of the latter per mole of the former. It is suitable to conduct the reaction at room temperature to about 100° C. for about 1 to about 10 hours. The phosgene for use in the above reaction includes trichloromethyl chloroformate (TCF) which produces phosgene.

The carbamoyl chloride represented by the formula (V) and thus obtained can be subsequently reacted with the imidazole (VI) without purification. This reaction is conducted in the same solvent as used for the first reaction. Preferably, the reaction is conducted using a hydrochloric acid removing agent which is the same base agent mentioned above or imidazole as converted to an alkali metal salt. The compound of the formula (V) and the base agent are used in the ratio of about 1 to about 10 moles, preferably about 1 to about 5 moles, of the latter per mole of the former. The compound of the formula (V) and the imidazole (VI) are used in the ratio of about 1 to about 10 moles, preferably about 1 to about 5 moles, of the latter per mole of the former. The reaction can be conducted at room temperature to about 150° C. for about 1 to about 10 hours.

The compound of the formula (II) for use as the starting material in the processes of the schemes (1) and (2) can be easily prepared by the process represented by the following reaction scheme (3).

Reaction scheme (3)

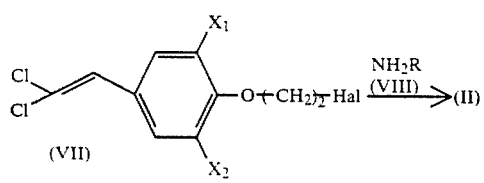

wherein R, $X^1$ and $X^2$ are as defined above, and Hal is a halogen atom.

The above reaction is conducted in a solvent or without using any solvent. Examples of useful solvents are ethers such as diethyl ether, dibutyl ether, tetrahydrofuran and dioxane, aliphatic hydrocarbon halides such as methylene chloride, chloroform and carbon tetrachloride, aromatic solvents such as benzene, toluene and xylene, ethyl acetate, dimethylformamide, dimethyl sulfoxide, etc. The reaction can be conducted also in the two-layer system of such a solvent and water. A base agent is used for this reaction as a hydrogen halide removing agent. Examples of useful base agents are alkali metal salts such as sodium hydroxide, potassium hydroxide, sodium carbonate, potassium carbonate, sodium hydrogencarbonate and potassium hydrogencarbonate, tertiary amines such as triethylamine and diethylaniline, pyridines, amines represented by the formula (VIII) for use as the other starting material, etc. The compound of the formula (VII) and the base agent are used in the ratio of about 1 to about 10 moles, preferably about 1 to about 5 moles, of the latter per mole of the former. The compound of the formula (VII) and the compound of the formula (VIII) are used in the ratio of about 1 to about 10 moles, preferably about 1 to about 5 moles, of the latter per mole of the former. The reaction is conducted at room temperature to about 200° C. for about 1 to about 10 hours.

The desired compound obtained by the above processes can be easily isolated and purified by usual methods, for example, solvent extraction, solvent dilution, recrystallization and column chromatography. In this way, the desired imidazole derivative represented by the formula (I) can be obtained with a high purity.

The compounds of the present invention have excellent control effects on various crop pathogens, for example, of blast (*Pyricularia oryzae*), helminthosporium leaf spot (*Ophiobolus miyabeanus*), bakanae disease (*Gibberella fujikuroi*), sclerotinia rat (*Sclerotinia sclerotiorum*), alternaria leaf spot (*Alternaria brassicae*), powdery mildew (*Sphaerotheca fuliginea*), gray mold (*Botrytis cinerea*), anthracnose (*Colletotrichum lagenarium*), eyespot (*Pseudocercosporella herpotrichoides*), etc. Moreover, the compounds of the invention exhibits no phytotoxicity at a concentration required for controlling these pathogens. Accordingly, the compound of the invention are used as fungicides for application to cereals, vegetables, vine, fruit trees and the like and also for seed treatment of cereals, vegetables and the like.

For use as such a control or fungicidal agent, the present compound may be used as it is, while it is generally used in the form of any preparation as admixed with auxiliary agents which are commonly used for formulating agricultural chemical preparations. Preferably, the compound is used in the form of an emulsion, wettable powder, dust or granules. Examples of useful auxiliary agents for assuring improved effects are extenders such as kieselguhr, kaolin, clay, bentonite, white carbon and talc, nonionic or anionic surfactants such as polyoxyethylene alkyl ether, polyoxyethylene alkyl phenyl ether, polyoxyethylene sorbitan fatty acid ester, polyoxyethylene fatty acid ester, sodium alkylbenzenesulfonate, sodium lignosulfonate, sodium alkylsulfate and sodium polyoxyethylenealkylsulfate, organic solvents such as benzene, toluene, xylene, acetone, cyclohexanone, methanol, ethanol, isopropyl alcohol, dioxane, dimethylformamide, dimethyl sulfoxide and carbon tetrachloride, etc.

The fungicidal composition of the present invention is prepared by admixing such an auxiliary agent with the present compound as its active component so that the composition contains usually about 0.1 to about 95 wt. %, preferably about 0.5 to about 70 wt. %, of the compound. The dosage is widely variable according to the type of composition, method and timing of application, kind of disease to be treated, weather condition, soil condition, etc. and is suitably determined. Generally, the composition is used at a concentration of about 1 to about 5000 ppm, preferably about 10 to about 3000 ppm, calculated as the active component.

When required, the fungicidal composition may have incorporated therein other agricultural chemicals such as insecticides, fungicides, miticides, nematicides, virucides, herbicides, plant growth regulators and attractants, fertilizers, etc.

EXAMPLES

The present invention will be described below with reference to preparation examples of compounds of the invention, and formulation examples and test examples with use of some of the compounds.

PREPARATION EXAMPLE 1

Preparation of 1-{N-[2-[2,6-dichloro-4-($\beta$,$\beta$-dichloro-vinyl)phenoxy]ethyl]-N-propylcarbamoyl}imidazole (Compound 1)

A 7.35 g quantity of 2-[2,6-dichloro-4-($\beta$, $\beta$-dichlorovinyl)phenoxy]ethyl bromide was dissolved in 100 ml of benzene, and 22.4 g of n-propylamine was added to the solution. The mixture was stirred at room temperature for 12 hours, and an excess of n-propylamine was distilled off. With addition of water, the residue was subjected to extraction with methylene chloride. The extract was washed with 5% aqueous solution of sodium hydrogencarbonate and then with water, dried over anhydrous magnesium sulfate and distilled in a vacuum to remove the solvent, giving 6.80 g of N-{2-[2,6-dichloro-4-($\beta$, $\beta$-dichlorovinyl)phenoxy]ethyl}-N-propylamine as a residue.

To the residue were added 100 ml of ethyl acetate and 3.2 g of N,N'-carbonyldiimidazole, and the mixture was stirred for 3 hours under reflex. The resulting mixture was cooled, then washed with water, dried over anhydrous magnesium sulfate and distilled to remove the ethyl acetate, giving 7.1 g of the desired compound represented by the following formula

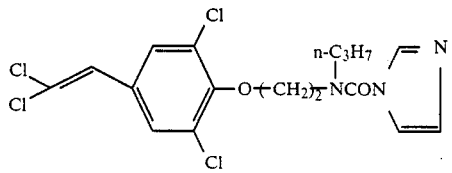

Yellow, oily.
$^1$H-NMR (CDCl$_3$) ; $\delta$ppm=0.7-1.90 (5H), 3.38-3.70 (2H), 3.70-3.94 (2H), 4.08-4.22 (2H), 6.60 (1H), 6.98 (1H), 7.22 (1H), 7.36 (2H), 7.82 (1H),

PREPARATION EXAMPLE 2

Preparation of 1-{N-[2-[2,6-dichloro-4-($\beta$, $\beta$-dichlorovinyl)phenoxy]ethyl]-N-(2-methoxy)ethylcarbamoyl}imidazole (Compound 2)

To 7.35 g quantity of 2-[2,6-dichloro-4-($\beta$, $\beta$-dichlorovinyl)phenoxy]ethyl bromide was added 15.1 g of 2-methoxyethylamine. The mixture was stirred at room temperature for 6 hours, further stirred under reflux for 2 hours and thereafter distilled to remove an excess of 2-methoxyethylamine. With addition of water, the residue was subjected to extraction with methylene chloride, and the extract was washed first with 5% aqueous solution of sodium hydrogencarbonate and then with water, dried over anhydrous magnesium sulfate and distilled in a vacuum to remove the solvent, giving 7.0 g of N-{2-[2,6-dichloro-4-($\beta$, $\beta$-dichlorovinyl)phenoxy[ethyl}-N-(2-methoxy)ethylamine as a residue.

To the residue were added 100 ml of ethyl acetate and 2.1 g of triethylamine, the mixture was cooled to not higher than 10° C, and a solution of 2.0 g of trichloromethyl chloroformate (TCF) in 10 ml of ethyl acetate was added dropwise to the mixture. The mixture was then stirred at room temperature for 2 hours. With addition of 1.4 g of imidazole and 2.1 g of triethylamine, the mixture was stirred under reflux for 3 hours. The mixture was cooled, then washed with water, dried over anhydrous magnesium sulfate and distilled to remove the ethyl acetate, giving 7.3 g of the desired compound represented by the following formula

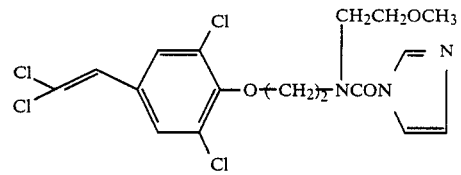

Yellow, oily.
$^1$H-NMR (CDCl$_3$) ; $\delta$ppm =3.30 (3H), 3.48–4.30 (8H), 6.60 (1H), 7.0 (1H), 7.20 (1H), 7.32 (2H), 7.78 (1H).

PREPARATION EXAMPLES 3–29

Compounds of Preparation Examples 3–29 (Compounds 3–29) were prepared in the same manner as in Preparation Examples 1 and 2. Table 1 shows the properties and NMR data of the compounds obtained.

TABLE 1

| Compd. No. | Structural formula |
|---|---|
| 3 | Cl-substituted phenyl—O-(CH$_2$)$_2$—NCON(CH$_3$)(imidazole) |
| 4 | Cl-substituted phenyl—O-(CH$_2$)$_2$—NCON(C$_2$H$_5$)(imidazole) |
| 5 | Cl-substituted phenyl—O-(CH$_2$)$_2$—NCON(n-C$_3$H$_7$)(imidazole) |
| 6 | Cl-substituted phenyl—O-(CH$_2$)$_2$—NCON(n-C$_4$H$_9$)(imidazole) |

TABLE 1-continued
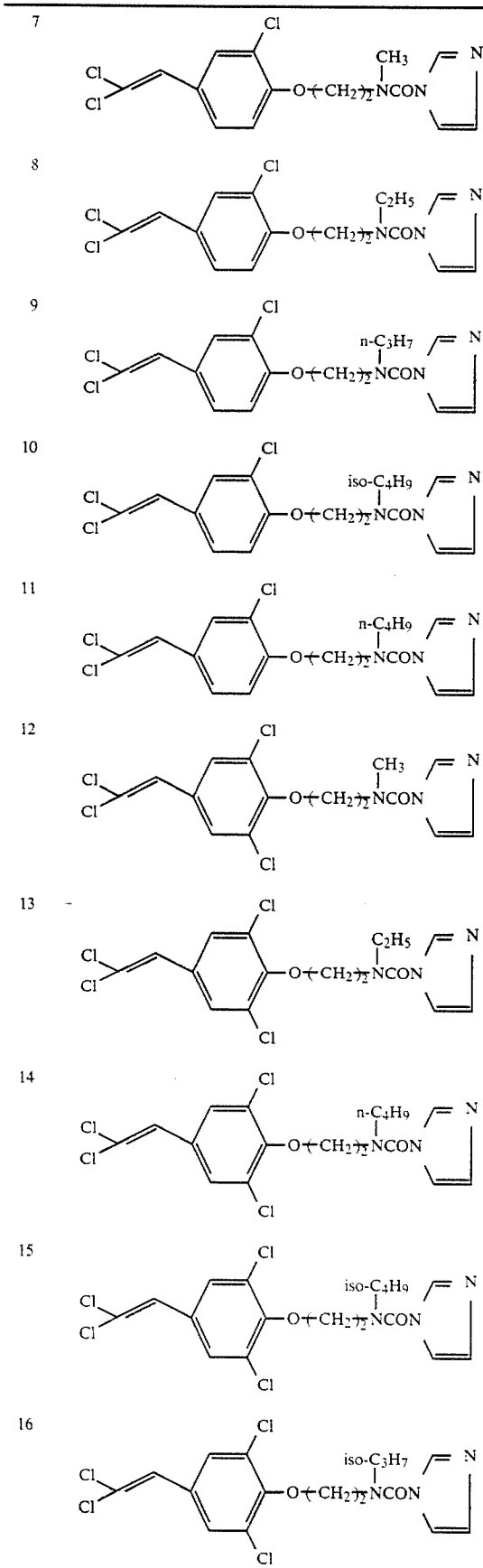
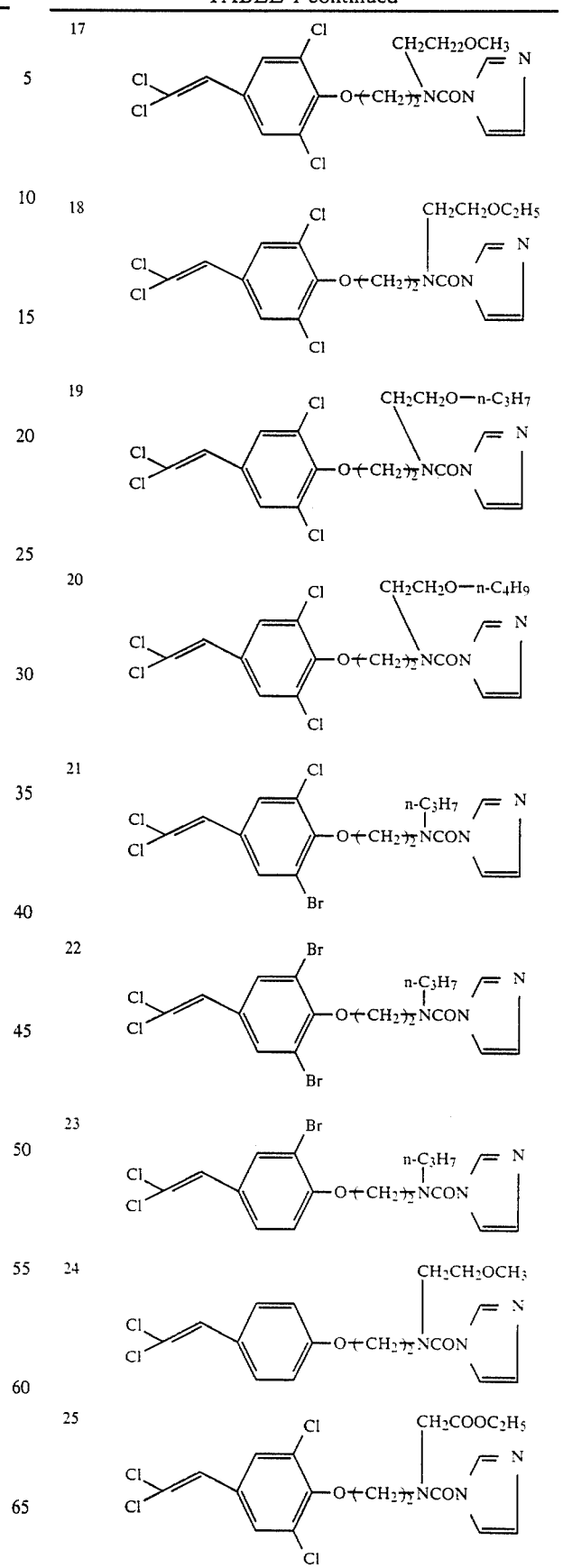

TABLE 1-continued

| Compd. No. | Structure | 
|---|---|
| 26 | Cl₂C=CH–C₆H₂(Cl)₂–O–(CH₂)₂–N(CH₂COOCH₃)–CON–(pyrrole) |
| 27 | Cl₂C=CH–C₆H₂(Cl)₂–O–(CH₂)₂–N(CH₂COO-n-C₃H₇)–CON–(pyrrole) |
| 28 | Cl₂C=CH–C₆H₂(Cl)₂–O–(CH₂)₂–N(CH₂COO-n-C₄H₉)–CON–(pyrrole) |
| 29 | Cl₂C=CH–C₆H₂(Cl)₂–O–(CH₂)₂–N(CH₂CN)–CON–(pyrrole) |

| Compd. No. | Property | $^1$H-NMR data |
|---|---|---|
| 3 | yellow oily | 3.12(3H), 3.60–3.90(2H), 4.0–4.30(2H), 6.62(1H), 6.70–7.42(6H), 7.78(1H) |
| 4 | yellow oily | 1.22(3H), 3.40(2H), 3.52–3.72(2H), 3.96–4.24(2H), 6.60(1H), 6.68–7.42(6H), 7.80(1H) |
| 5 | yellow oily | 0.90(3H), 1.40–1.90(2H), 3.20–3.52(2H), 3.58–3.84(2H), 4.0–4.26(2H), 6.60(1H), 6.68–7.42(6H), 7.78(1H) |
| 6 | yellow oily | 0.70–2.0(7H), 3.30–4.22(6H), 6.60(1H), 6.68–7.42(6H), 7.78(1H) |
| 7 | yellow oily | 3.12(3H), 3.60–3.90(2H), 4.0–4.30(2H), 6.60(1H), 6.70–7.30(5H), 7.80(1H) |
| 8 | yellow oily | 1.22(3H), 3.40(2H), 3.52–3.72(2H), 3.96–4.24(2H), 6.60(1H), 6.70–7.30(5H), 7.80(1H) |
| 9 | yellow oily | 0.90(3H), 1.40–1.90(2H), 3.20–3.52(2H), 3.58–3.84(2H), 4.0–4.26(2H), 6.60(1H), 6.70–7.30(5H), 7.80(1H) |
| 10 | yellow oily | 0.90(6H), 1.70–2.2(1H), 3.22(2H), 3.60–3.90(2H), 3.96–4.26(2H), 6.60(1H), 6.70–7.42(5H), 6.72(1H) |
| 11 | yellow oily | 0.70–2.0(7H), 3.30–4.22(6H), 6.60(1H), 6.70–7.30(5H), 7.78(1H) |
| 12 | yellow oily | 3.12(3H), 3.60–3.90(2H), 4.0–4.30(2H), 6.60(1H), 7.0(1H), 7.20(1H), 7.32(2H), 7.80(1H) |
| 13 | yellow oily | 1.22(3H), 3.40(2H), 3.52–3.72(2H), 3.96–4.24(2H), 6.60(1H), 6.98(1H), 7.20(1H), 7.32(2H), 7.80(1H) |
| 14 | yellow oily | 0.70–2.0(7H), 3.30–4.22(6H), 6.60(1H), 7.0(1H), 7.20(1H), 7.32(2H), 7.82(1H) |
| 15 | yellow oily | 0.90(6H), 1.70–2.2(1H), 3.22(2H), 3.60–3.90(2H), 3.96–4.26(2H), 6.60(1H), 7.0(1H), 7.20(1H), 7.34(2H), 7.80(1H) |
| 16 | yellow oily | 0.92(6H), 2.62–2.80(1H), 3.60–3.90(2H), 4.0–4.28(2H), 6.60(1H), 7.0(1H), 7.20(1H), 7.34(2H), 7.80(1H) |
| 17 | yellow oily | 1.70–2.20(2H), 3.24(3H), 3.30–3.94(6H), 4.06–4.30(2H), 6.60(1H), 7.0(1H), 7.20(1H), 7.34(2H), 7.86(1H) |
| 18 | yellow oily | 1.20(3H), 3.20–4.30(10H), 6.60(1H), 7.0(1H), 7.20(1H), 7.32(1H), 7.80(1H) |
| 19 | yellow oily | 0.92(3H), 1.20–1.80(2H), 3.20–4.30(10H), 6.60(1H), 7.0(1H), 7.20(1H), 7.32(2H), 7.80(1H) |
| 20 | yellow oily | 0.72–1.80(5H), 3.20–4.30(10H), 6.60(1H), 7.0(1H), 7.20(1H), 7.34(2H), 7.80(1H) |
| 21 | yellow oily | 0.7–1.90(5H), 3.38–3.70(2H), 3.70–3.94(2H), 4.1–4.22(2H), 6.60(1H), 7.0(1H), 7.20(1H), 7.32(2H), 7.80(1H) |
| 22 | yellowish brown oily | 0.7–1.90(5H), 3.38–3.68(2H), 3.72–3.94(2H), 4.1–4.22(2H), 6.60(1H), 7.0(1H), 7.20(1H), 7.34(2H), 7.80(1H) |
| 23 | yellowish brown oily | 0.90(3H), 1.40–1.90(2H), 3.20–3.52(2H), 3.58–3.84(2H), 4.0–4.26(2H), 6.60(1H), 6.70–7.30(5H), 7.78(1H) |
| 24 | yellow oily | 3.30(3H), 3.48–4.30(8H), 6.60(1H), 6.70–7.42(6H), 7.78(1H) |
| 25 | yellow oily | 1.28(3H), 3.70–4.40(6H), 6.60(1H), 6.92(1H), 7.20(1H), 7.32(2H), 7.82(1H) |
| 26 | pale yellow oily | 3.70(3H), 3.72–4.0(2H), 4.08–4.30(2H), 4.32(2H), 6.60(1H), 6.92(1H), 7.20(1H), 7.32(2H), 7.82(1H) |
| 27 | yellow oily | 0.70–1.80(5H), 3.72–4.40(8H), 6.60(1H), 6.98(1H), 7.20(1H), 7.32(1H), 7.86(1H) |
| 28 | yellow oily | 0.70–1.82(7H), 3.72–4.40(8H), 6.60(1H), 6.98(1H), 7.20(1H), 7.34(2H), 7.82(1H) |
| 29 | yellow oily | 3.70–4.0(2H), 4.10–4.30(2H), 4.32(2H), 6.60(1H), 6.98(1H), 7.2(1H), 7.34(2H), 7.86(1H) |

FORMULATION EXAMPLE 1 (20% wettable powder)

| | Parts by weight |
|---|---|
| Compound 1 | 20 |
| Kieselguhr | 12 |
| Clay | 63 |
| Sodium alkylbenzenesulfonate | 2 |
| Sodium salt of alkylnaphthalenesulfonic acid-formalin condensation product | 3 |

-continued

| | Parts by weight |
|---|---|
| | 100 |

The above ingredients were thoroughly mixed together by a mixer and finely divided by a pulverizer to obtain a 20% wettable powder.

FORMULATION EXAMPLE 2 (30% emulsifiable concentrate)

| | Parts by weight |
|---|---|
| Compound 5 | 30 |
| Polyoxyethylene alkyl phenyl ether | 8 |
| Calcium alkylbenzenesulfonate | 7 |
| Xylene | 55 |
| | 100 |

The above ingredients were mixed together to obtain a 30% emulsifiable concentrate.

FORMULATION EXAMPLE 3 (2% dust)

| | Parts by weight |
|---|---|
| Compound 1 | 2 |
| Particulate clay | 98 |
| | 100 |

The above ingredients were thoroughly mixed together to obtain 2% dust.

TEST EXAMPLE 1

Control effect on cucumber powdery mildew

An emulsifiable concentrate prepared in the same manner as in Formulation Example 2 was sprayed, as diluted to a specified concentration with water, onto cucumber seedlings in two-leaf stage planted in pots, 9 cm in diameter. One day after the application, a suspension of spores of *Sphaerotheca fulginea* causing the above disease was sprayed onto the seedlings for inoculation, and the seedlings were allowed to stand at 23° C. in a constant-temperature chamber. Ten days thereafter, the lesion area percentage was determined, the infection degree was determined from the percentate according to the criteria given below, and percent control effect was calculated from the following equation.

| Lesion area percentage | Infection degree |
|---|---|
| 0 | 0 |
| Up to 2 | 0.5 |
| 3–5 | 1 |
| 6–15 | 2 |
| 16–30 | 3 |
| 31–50 | 4 |
| At least 51 | 5 |

$$\text{Percent control effect} = \frac{A - B}{A} \times 100$$

where A is the infection degree of untreated group and B is the infection degree of treated group.

The seedlings were also checked for phytotoxicity. Table 2 shows the results.

TABLE 2

| Compound No. | Concentration (ppm) | Control effect (%) | Phytotoxicity |
|---|---|---|---|
| 1 | 100 | 100 | None |
| 5 | 100 | 97 | None |
| 6 | 100 | 98 | None |
| 9 | 100 | 100 | None |
| 11 | 100 | 100 | None |
| 13 | 100 | 97 | None |
| 14 | 100 | 100 | None |
| 15 | 100 | 100 | None |
| 18 | 100 | 100 | None |
| 25 | 100 | 98 | None |
| R-1* | 100 | 86 | None |

Note:
*Comparative Compound R-1 represented by the following formula.

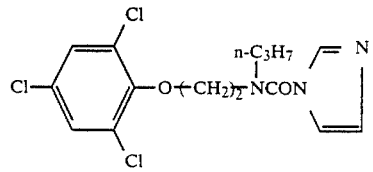

TEST EXAMPLE 2

Control effect on beat damping-off

A 100 g quantity of soil contaminated with *Rhizoctonia Solani* and a dust prepared in the same manner as in Formulation Example 3 were thoroughly mixed together to obtain soil containing a specified concentration of the compound. The soil was placed into a plastic pot. Ten beat seeds were sown in each of pots thus prepared. The pots were maintained at 24° C., and checked for the number of seedlings suffering from damping-off ten days later. The percent control effect was calculated from the following equation.

$$\text{Percent control effect} = \left(1 - \frac{\text{Percent damping-off of treated group}}{\text{Percent damping-off of untreated group}}\right) \times 100$$

Three pots were used as one group for testing, and the control effect was determined from the average percent damping-off of the three pots. The beets were also checked for phytotoxicity in the same manner as in Test Example 1.

Table 3 shows the results.

TABLE 3

| Compound No. | Concentration (ppm) | Control effect (%) | Phytotoxicity |
|---|---|---|---|
| 1 | 500 | 100 | None |
| 6 | 500 | 85 | None |
| 11 | 500 | 90 | None |
| 13 | 500 | 95 | None |
| 14 | 500 | 95 | None |
| 21 | 500 | 90 | None |
| 25 | 500 | 80 | None |

TABLE 3-continued

| Compound No. | Concentration (ppm) | Control effect (%) | Phytotoxicity |
|---|---|---|---|
| R-2* | 500 | 60 | None |

Note:
*Comparative Compound R-2 represented by the following formula.

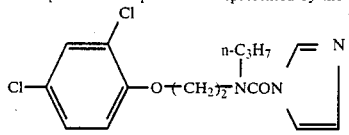

TEST EXAMPLE 3

Control effect on rice blast

A wettable powder prepared in the same manner as in Formulation Example 1 was sprayed, as diluted to a specified concentration, to paddy rice seedlings (variety: Asahi) in three-leaf stage grown by soil culture in pots 9 cm in diameter and placed in a greenhouse. One day after the application, a suspension of spores of *Pyricularia oryzae* was sprayed onto the seedlings for inoculation. The seedlings were then allowed to stand overnight at a humidity of 95 to 100% and a temperature of 24° to 25° C. Five days after the inoculation, the seedlings were checked for the number of blast lesions per leaf, and the percent control effect was calculated from the following equation.

Percent control effect =

$$\left(1 - \frac{\text{Number of lesions of treated group}}{\text{Number of lesions of untreated group}}\right) \times 100$$

The seedlings were also checked for phytotoxicity. Table 4 shows the results.

TABLE 4

| Compound No. | Concentration (ppm) | Control effect (%) | Phytotoxicity |
|---|---|---|---|
| 1 | 500 | 100 | None |
| 2 | 500 | 90 | None |
| 13 | 500 | 100 | None |
| 14 | 500 | 100 | None |
| 15 | 500 | 100 | None |
| 22 | 500 | 97 | None |
| 26 | 500 | 93 | None |
| 29 | 500 | 90 | None |
| R-2 | 500 | 37 | None |

TEST EXAMPLE 4

Control effect on rice bakanae disease (seed treatment)

For disinfection, rice seeds spontaneously infected with *Gibberella fujikuroi* were immersed in a dispersion of wettable powder prepared in the same manner as in Formulation Example 1 and having a specified concentration. The seeds were thereafter dried in air, sown in a rice seedling box and then maintained in the usual manner. The seedlings were checked for infection by sampling from time to time during the period of 20 days following the sowing, and the percent control effect was calculated from the following equation.

Percent control effect =

$$\left(1 - \frac{\text{Infection ratio of treated group}}{\text{Infection ratio of untreated group}}\right) \times 100$$

The effect is expressed in terms of the average of three test groups, 300 grains in each group. The results are given in Table 5, which also shows the results obtained by checking the seedlings for phytotoxicity.

TABLE 5

| Compound No. | Concentration (ppm) | Control effect (%) | Phytotoxicity |
|---|---|---|---|
| 1 | 500 | 100 | None |
| 5 | 500 | 100 | None |
| 6 | 500 | 99.1 | None |
| 9 | 500 | 100 | None |
| 11 | 500 | 100 | None |
| 13 | 500 | 98.9 | None |
| 14 | 500 | 100 | None |
| 21 | 500 | 100 | None |
| 22 | 500 | 100 | None |
| 25 | 500 | 100 | None |
| R-1 | 250 | 100 | Delayed germination Inhibited growth |

TEST EXAMPLE 5

Control effect on rice helminthosporium leaf spot (seed treatment)

For testing, unhulled rice grains spontaneously infected with *Cochliobolus miyabeanus* were collected from a field. The seeds were disinfected and further handled in the same manner as in Test Example 4. The onset of the disease was checked by counting the number of infected seedlings 20 days after the sowing, and the percent disinfection of seeds was calculated in the same manner as in Test Example 4. The seedlings were also checked for phytotoxicity. Table 6 shows the average percent disinfection values obtained and the results of phytotoxicity check.

TABLE 6

| Compound No. | Concentration (ppm) | Control effect (%) | Phytotoxicity |
|---|---|---|---|
| 1 | 500 | 100 | None |
| 5 | 500 | 98 | None |
| 6 | 500 | 92 | None |
| 9 | 500 | 90 | None |
| 11 | 500 | 100 | None |
| 13 | 500 | 100 | None |
| 14 | 500 | 100 | None |
| 21 | 500 | 98 | None |
| 22 | 500 | 90 | None |
| R-1 | 500 | 90 | Delayed germination Inhibited growth |

We claim:

1. An imidazole derivative represented by the formula

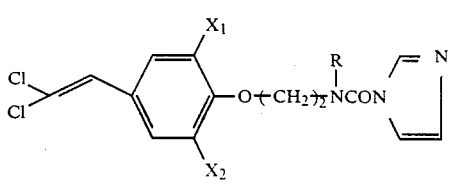

wherein R is lower alkyl, lower alkoxyalkyl, lower alkoxycarbonylmethyl or cyanomethyl, and $X^1$ and $X^2$ are each a hydrogen atom or halogen atom.

2. An imidazole derivative as defined in claim 1 wherein R is lower alkyl.

3. An imidazole derivative as defined in claim 2 wherein R is n-propyl.

4. An imidazole derivative as defined in claim 1 wherein $X^1$ and $X^2$ are each a halogen atom.

5. An imidazole derivative as defined in claim 4 wherein $X^1$ and $X^2$ are each a chlorine atom.

6. An imidazole derivative as defined in claim 1 which is 1-{N-[2-[2,6-dichloro-4-(β, β-dichlorovinyl)phenoxy]ethyl]-N-propylcarbamoyl}imidazole represented by the formula

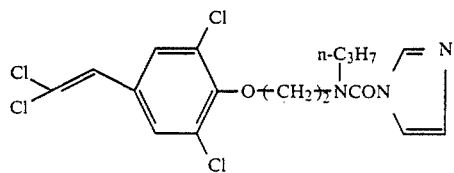

7. A fungicidal composition for agricultural and horticultural uses comprising an inert carrier and a fungicidally effective amount of an imidazole derivative defined in claim 1 as an active component thereof.

* * * * *